United States Patent [19]
Wiggins

[11] Patent Number: 6,040,132
[45] Date of Patent: Mar. 21, 2000

[54] METHODS FOR THE LYOPHILIZATION OF LIVING BIOLOGICAL MATERIALS

[75] Inventor: Philippa M. Wiggins, Mairangi Bay, New Zealand

[73] Assignee: Biostore New Zealand, Ltd., Parnell, New Zealand

[21] Appl. No.: 09/085,334

[22] Filed: May 26, 1998

Related U.S. Application Data

[63] Continuation-in-part of application No. 09/060,770, Apr. 15, 1998, which is a continuation-in-part of application No. 08/989,470, Dec. 12, 1997, Pat. No. 5,962,213, which is a continuation-in-part of application No. 08/842,553, Apr. 15, 1997, which is a continuation-in-part of application No. 08/722,306, Sep. 30, 1996, Pat. No. 5,827,640, which is a continuation-in-part of application No. 08/662,244, Jun. 14, 1996, Pat. No. 5,879,875.

[51] Int. Cl.[7] .......................................... A01N 1/02
[52] U.S. Cl. .................................. 435/2; 435/1.3
[58] Field of Search .......................... 435/2, 1.3

[56] References Cited

U.S. PATENT DOCUMENTS

| | | | |
|---|---|---|---|
| 4,370,348 | 1/1983 | Shriver | 424/331 |
| 4,380,582 | 4/1983 | Orlando et al. | |
| 5,045,446 | 9/1991 | Goodrich, Jr. et al. | |
| 5,242,792 | 9/1993 | Rudolph et al. | |
| 5,580,856 | 12/1996 | Prestrelski et al. | |
| 5,702,880 | 12/1997 | Segall et al. | 435/1.2 |
| 5,733,894 | 3/1998 | Segall et al. | 514/59 |
| 5,827,640 | 10/1998 | Wiggins et al. | 435/1.1 |

FOREIGN PATENT DOCUMENTS

| | | |
|---|---|---|
| 9118504 | 12/1991 | WIPO . |
| WO 92/18136 | 10/1992 | WIPO . |
| 9300807 | 1/1993 | WIPO . |
| 9314191 | 7/1993 | WIPO . |

OTHER PUBLICATIONS

Clark, M.E., et al., "Studies on Water in Barnacle Muscle Fibres II. Role of Ions and Organic Solutes in Swelling of Chemically–Skinned Fibres", *J. exp. Biol.*, vol. 90, pp. 43–63 (1981).

Arakawa, T. et al., Advanced Drug Delivery Reviews, vol. 10(1), p. 1–28, 1993.

*Primary Examiner*—Sandra E. Saucier
*Attorney, Agent, or Firm*—Ann W. Speckman; Janet Sleath

[57] ABSTRACT

The present invention provides methods for preserving living biological materials by lyophilization that enable cells and tissues to be stored for extended periods of time with minimal loss of biological activity. In one embodiment, the inventive methods comprise contacting a biological material with a preservative solution comprising either betaine or trimethyl amine oxide, together with sodium citrate and sodium chloride, reducing the temperature of the biological material to less than 0° C., and drying the biological material to provide a freeze-dried material. The preservative solutions employed in the inventive methods are preferably isotonic with the material to be preserved and substantially free of iodide, dihydrogen phosphate, bicarbonate, nitrate and bisulfate.

15 Claims, 7 Drawing Sheets

METHODS FOR THE LYOPHILIZATION OF LIVING BIOLOGICAL MATERIALS

REFERENCE TO RELATED APPLICATIONS

This application is a continuation-in-part of U.S. application No. 09/060,770, filed Apr. 15, 1998, which is a continuation-in-part of U.S. application Ser. No. 08/989,470, filed Dec. 12, 1997, now U.S. Pat. No. 5,962,213, which is a continuation-in-part of U.S. application Ser. No. 08/842,553, filed Apr. 15, 1997, which is a continuation-in-part of U.S. application Ser. No. 08/722,306, filed Sep. 30, 1996, now U.S. Pat. No. 5,827,640, which is a continuation-in-part of U.S. application Ser. No. 08/662,244, filed Jun. 14, 1996, now U.S. Pat. No. 5,879,875.

TECHNICAL FIELD OF THE INVENTION

This invention relates to the field of preserving living biological materials and, more particularly, to methods for the preservation of living cells and tissues by lyophilization.

BACKGROUND OF THE INVENTION

Methods for the preservation of living biological materials are employed in many clinical and veterinary applications wherein living material, including cells, tissues and organs, is harvested and stored in vitro for some period of time before use. Examples of such applications include whole blood transplants, platelet transplants, autologous and allogeneic bone marrow transplants, organ storage and transplants, embryo transfer, artificial insemination, in vitro fertilization, skin grafting and storage of tissue biopsies for diagnostic purposes. Preservation techniques are also important in the storage of cell lines for experimental use in hospital, industrial, university and other research laboratories.

Methods currently employed for the preservation of cellular biological materials include immersion in saline-based media; storage at temperatures slightly above freezing; storage at temperatures of about −80° C.; storage in liquid nitrogen at temperatures of about −196° C.; and freeze-drying or lyophilization. The goal of all these techniques is to store living biological materials for an extended period of time with minimal loss of normal biological structure and function.

Saline-based media employed in the preservation of living biological materials typically consist of isotonic saline (sodium chloride 0.154M) which has been modified by the addition of low concentrations of various inorganic ions such as-potassium, calcium, magnesium, chloride, phosphate and bicarbonate to mimic the extracellular environment. Small amounts of compounds such as glucose, amino acids and vitamins are often added as metabolites. Examples of media currently employed for the preservation of biological materials include phosphate-buffered saline (PBS), M-2 (a Hepes buffered murine culture medium), Ringer's solution and Krebs bicarbonate-buffered medium. The viability of biological materials stored in saline-based media above 0° C. gradually decreases over time; living tissues can only be successfully preserved for relatively short periods of time.

When employing freezing techniques to preserve biological materials, high concentrations (approximately 10% by volume) of cryoprotectants, such as glycerol, dimethylsulfoxide (DMSO), glycols or propanediol, are often introduced to the material prior to freezing in order to limit the amount of damage caused to cells by the formation of ice crystals during freezing. The choice and concentration of cryoprotectant, time-course for the addition of cryoprotectant and temperature at which the cryoprotectant is introduced all play an important role in the success of the preservation procedure. Furthermore, in order to reduce the loss of cells, it is critical that such variables as the rate and time-course of freezing, rate and time-course of thawing and further warming to room or body temperature, and replacement of cryoprotectant solution in the tissue mass with a physiological saline solution be carefully controlled. The large number of handling steps required in freezing techniques increases the loss of cells. The freezing techniques currently employed in the preservation of biological materials are both technically demanding and time consuming. Other disadvantages of preserving biological materials by conventional freezing methods include: reduction of cell viability; toxic effects of the cryoprotectant to the patient upon re-infusion; the high costs of processing and storage; and the difficulty of transporting frozen materials.

For example, the use of conventional freezing methods in the preservation of platelets results in a progressive deterioration in cell function to such a degree that platelets are typically stored at room temperature. However, due to the risk of bacterial contamination, platelet storage at room temperature is generally restricted to five days. As a result, approximately 20% of transfusable platelet units must be discarded.

The high costs associated with maintaining preserved biological materials at freezing temperatures, together with the problems associated with transporting frozen materials, can be avoided by lyophilization, or freeze-drying. Lyophilized materials can be stored at room temperature for extended periods of time and then readily reconstituted for use. However, while proteins have been successfully preserved by lyophilization, this technique has to date been of limited use in the preservation of whole cells.

U.S. Pat. No. 5,242,792 describes a method for the lyophilization of red blood cells which includes contacting the cells with a protective agent selected from the group consisting of either sucrose, raffinose, maltose, lactose or trehalose in a buffered solution and permeabilizing the cells by contacting them with either inositol or glycerol prior to freezing and lyophilizing. International Patent Application No. WO 93/00807 discloses an additive for stabilizing biological materials during lyophilization including a cryoprotectant, such as polyethylene glycol, and a second component such as a sugar, polyhydroxyl alcohol, amino acid or methylamine. U.S. Pat. No. 5,045,446 teaches a method for lyophilizing cells which employs a solution comprising monosaccharide hexoses and pentoses, and a mixture of at least two amphipathic polymers. International Patent Application No. WO 93/14191 teaches a process for freezing or freeze-drying cells which uses a cryoprotectant medium having an elevated glass transition temperature.

SUMMARY

The present invention provides methods for lyophilizing living biological materials, such as platelets, platelet membranes and red blood cells, that enables them to be stored in an inactive, desiccated state at room temperature for extended periods of time with minimal loss of biological activity. Such methods comprise contacting, preferably immersing, the biological material to be preserved in one or more of the preservative solutions discussed below. The solution containing the biological material is then rapidly cooled to a temperature of less than about −80° C., more preferably less than about −140° C., and most preferably to a temperature of about −196° C., and dried to provide a freeze-dried material. The cooled material is preferably dried by sublimation under a high vacuum to provide a freeze-dried material having less than about 5%, more preferably less than about 1% by weight of residual water. In one embodiment of the present invention, the biological material is cooled rapidly following immersion in the preservative solution, most preferably by plunging into liquid nitrogen, and is dried under conditions which minimize increases in temperature before the removal of water is complete.

The preservative solutions employed in the inventive methods are generally isotonic with the biological material to be preserved and are substantially free of iodide, dihydrogen phosphate, bicarbonate, nitrate and bisulfate. The solutions comprise either betaine or trimethyl amine oxide, and may also include sodium chloride. In one preferred embodiment, the preservative solutions comprise either betaine or trimethyl amine oxide, together with sodium citrate and sodium chloride, with the betaine or TMAO preferably being present at a concentration greater than about 150 mM or less than 220 mM, more preferably between about 150 mM and about 220 mM, and most preferably at a concentration of about 187 mM for betaine or 184 mM for TMAO; the sodium citrate preferably being present at a concentration greater than about 1.5 mM or less than about 2.5 mM, more preferably between about 1.5 mM and about 2.5 mM, and most preferably at a concentration of about 1.96 mM; and the sodium chloride preferably being present at a concentration greater than about 35 mM or less than about 55 mM, more preferably between about 35 mM and about 55 mM, and most preferably at a concentration of about 45.8 mM.

In a second preferred embodiment, the preservative solutions employed in the inventive methods comprise either betaine or TMAO, together with sodium chloride and calcium chloride. Preferably, such solutions comprise betaine or TMAO at a concentration greater than about 150 mM or less than about 220 mM, more preferably at a concentration between about 150 mM and 220 mM, and most preferably at a concentration of about 188 mM; calcium chloride at a concentration greater than about 1.5 mM or less than about 2.0 mM, more preferably between about 1.5 and 2.0 mM, and most preferably at a concentration of about 1.75 mM; and sodium chloride at a concentration greater than about 35 mM or less than about 55 mM, more preferably between about 35 mM and about 55 mM, and most preferably at a concentration of about 45.8 mM.

As detailed below, it has been found that the methods of the present invention can be employed to maintain the viability of living biological materials at room temperature indefinitely. The ability to preserve biological materials without the need for storage at temperatures below freezing and for longer periods of time than are generally possible with conventional preservation methods, provides vastly improved storage and transport times for biological materials for use in applications such as blood and platelet transfusions.

The preservation methods of the present invention are less complex than many of the methods typically employed for the preservation of living biological materials, thereby reducing costs and increasing the ease of use and availability of preservation procedures. Furthermore, the compositions employed in the inventive methods are of low toxicity, resulting in fewer negative side effects when biological materials, such as platelets, are returned to a patient.

The above-mentioned and additional features of the present invention and the manner of obtaining them will become apparent, and the invention will be best understood by reference to the following more detailed description, read in conjunction with the accompanying drawings.

DETAILED DESCRIPTION

Figure 1A:
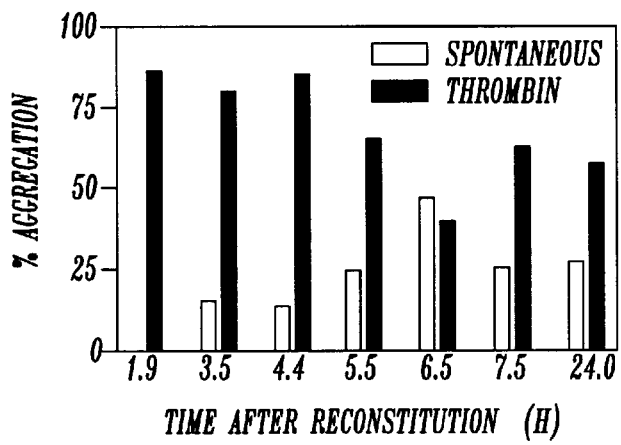
FIGS. 1A and B illustrate the percentage thrombin-activated aggregation and percentage recovery, respectively, over time of reconstituted platelets following lyophilization in a solution of TMAO, sodium chloride and sodium citrate (referred to as Solution 70/30c2).

The present invention provides lyophilization methods which may be used in the preservation of living biological materials including mammalian, plant and marine cells, cell lines, tissues and organs. As used herein the term "lyophilization" refers to the process of freezing a substance and then reducing the concentration of water, by sublimation and/or evaporation to levels which do not support biological or chemical reactions.

When a living biological material is preserved, its viability is maintained in vitro for an extended period of time, such that the material resumes its normal biological activity on being removed from storage. During storage the biological material is thus maintained in a reversible state of dormancy, with metabolic activity being substantially lower than normal. Examples of mammalian biological materials which may be preserved using the present invention include, but are not limited to, cells and tissues such as platelets, platelet membranes, red blood cells, whole blood, haematopoietic stem cells, bone marrow, embryos, osteoblasts, spermatozoa, granulocytes, dendritic cells, oocytes and various cell lines established in tissue culture. In addition to the preservation of human biological materials, the inventive methods may also be employed in veterinary applications, and for preservation of plant and marine tissues.

In the preservative methods of the present invention, biological materials to be preserved are harvested using standard techniques and contacted, preferably immersed, in one of the aqueous preservative solutions discussed below, preferably at about 4° C. The biological material is then cooled to a temperature below freezing and dried by means of sublimation and/or evaporation. Methods and apparatus for the lyophilization, or freeze-drying, of materials are well known to those of skill in the art and include, for example, those discussed by Pohl (Pohl T. (1990) "Concentration of proteins and removal of solutes" in *Guide to Protein Purification,* ed. Deutscher MP, Academic Press, San Diego, Calif., USA).

In a preferred embodiment of the present invention, the temperature of the immersed biological material is reduced to below freezing as rapidly as possible. More preferably the temperature of the immersed material is reduced from about 4° C. to below about −80° C., preferably to below about −140° C. This may be accomplished by placing the uninsulated material in a −140° C. freezer or, more preferably, by plunging it into liquid nitrogen at −196° C. The frozen biological material is subsequently dried using a conventional lyophilizer, or freeze dryer, under conditions that minimize any increase in temperature, to provide a freeze-dried material having less than about 5% by weight, more preferably less than about 1% by weight, of residual water content. The resulting lyophilized biological material may be stored at room temperature for an indefinite period of time. Following storage, the lyophilized material is reconstituted, preferably by the addition of the same amount of water as was removed during drying or by adding the same volume of water in any desired isotonic solution (for example, saline).

The preservative solutions used in the lyophilization methods of the present invention may be in either a ready-to-use form or may be provided in a concentrated form, such as a solid, including for example, powder or tablets, which is reconstituted in water prior to use. The solutions may also be provided in a concentrated liquid form for dilution by the user. As with solutions employed in conventional preservation methods, the solutions are sterile.

The solutions employed in the inventive methods are substantially isotonic with the biological material to be preserved. Cells in an isotonic solution neither shrink nor swell substantially. Preferably, the preservative solutions have an osmolality substantially equal to that of the biological material to be preserved. As detailed below, it has been determined that an osmolality of between about 280 mOsM and about 320 mOsM is preferable for solutions for the preservation of mammalian biological materials. Osmolalities of between about 900 mOsM to about 1000 mOsM and between about 70 mOsM to about 80 mOsM are preferred for the preservation of marine and plant biological materials, respectively.

The preservative solutions may include oxyanions, such as dihydrogen phosphate, bicarbonate, nitrate, nitrite, bisulfate, chlorate, perchlorate, bromate, permanganate, iodate, periodate, trichloroacetate, bromoacetate and dihydrogen phosphite, at concentrations less than about $10^{-5}$M. However, it has been observed that the presence of univalent oxyanions or iodide ions in preservation solutions reduces the effectiveness of the preservative solutions. Thus the solutions are preferably substantially free of univalent oxyanions and of iodide. As used herein the term "substantially free" means that the concentration of ions is below that required to raise the metabolic activity of the material to be preserved during storage.

In one aspect, the solutions employed in the inventive methods comprise a first neutral solute having a molecular weight of at least about 335 and a solubility in water of at least about 0.3M (hereinafter referred to as Class I solutes), and a second neutral solute having a molecular weight of less than about 200 (hereinafter referred to as Class II solutes), the second neutral solute additionally having both hydrophilic and hydrophobic moieties. Class I solutes are generally too large to penetrate cells. Preferably, Class I solutes are disaccharides or trisaccharides. Examples of such solutes include raffinose, trehalose, sucrose and lactose, with raffinose and trehalose being preferred Class I solutes.

Class II solutes generally do not passively cross cell membranes, but may be actively taken up by some cells. They are used by many cells as intracellular osmolytes. Examples of such solutes include TMAO, betaine, taurine, sarcosine, glucose, mannose, fructose, ribose, galactose, sorbitol, mannitol and inositol. TMAO and betaine are the preferred Class II solutes for many biological materials.

In one embodiment, the solutions employed in the inventive methods comprise either (a) raffinose and TMAO, preferably in a molar ratio greater than about 1.1:1 or less than about 2.0:1, more preferably in a molar ratio of between about 1.4:1 to about 1.8:1 and most preferably in a molar ratio of about 1.6:1; (b) trehalose and TMAO, preferably in a molar ratio greater than about 1.1:1 or less than about 1.4:1, more preferably in a molar ratio of between about 1.1:1 and about 1.4:1 and most preferably about 1.3:1, (c) raffinose and betaine, preferably in a molar ratio of less than about 1.7:1 or greater than about 1.3:1, more preferably in a molar ratio of between about 1.3:1 and about 1.7:1, and most preferably in a molar ratio of between about 1.4:1 and about 1.6:1; or (d) trehalose and betaine, preferably in a molar ratio of less than about 1.7:1 or greater than about 1.3:1, more preferably in a molar ratio of between about 1.3:1 and about 1.7:1, and most preferably in a molar ratio of between about 1.4:1 and about 1.6:1.

The inventive solutions may additionally contain ions but, as noted above, are substantially free of univalent oxyanions and iodide. Other ionic species may be selected according to their ability to suppress metabolism during storage.

It has been determined that, with the exception of platelets, effective storage times for biological materials increase with the addition of calcium to the preservative compositions. Preferably the calcium is present as calcium sulfate or calcium chloride, and is present at a concentration greater than about 1.5 mM or less than about 2.0 mM, more preferably at a concentration of between about 1.5 mM and about 2.0 mM, and most preferably about 1.75 mM. The addition of either sodium sulfate, sodium citrate or sodium chloride also increases effective storage times for many biological materials.

In one embodiment, a solution comprising the following components has been found to be particularly effective in preserving many biological materials: between about 60% and about 80% by volume, preferably about 70%, of a solution of raffinose and TMAO; between about 40% and about 20% by volume, preferably about 30% of a solution of sodium sulfate; and about 1.75 mM calcium sulfate, wherein the raffinose and TMAO are present in a ratio of about 1.6:1, and wherein both the solution of raffinose and TMAO and the solution of sodium sulfate are isotonic with the material to be preserved. In this aspect, the concentrations of solutes are preferably as follows: TMAO about 70–75 mM, most preferably about 72 mM; raffinose about 120–130 mM, most preferably about 126 mM; sodium sulphate about 35–45 mM, most preferably about 39 mM; and calcium sulphate about 1.5–2.0 mM, most preferably about 1.75 mM.

The preservative solutions employed in the inventive methods may be conveniently prepared by first making individual solutions of the separate components, with each individual solution being of the desired osmolality. The individual solutions are then mixed in the desired proportions to provide the preservative solutions. For example, to prepare one preferred embodiment of the inventive solutions for the preservation of mammalian biological materials (referred to as Solution 70/30), solutions of TMAO, raffinose, sodium sulfate and calcium chloride having the following concentrations are first prepared:

| | |
|---|---|
| TMAO dihydrate | 29.7 g/l |
| raffinose | 147.1 g/l |
| anhydrous sodium sulfate | 18.6 g/l |
| calcium chloride dihydrate | 17.1 g/l |

Each of these solutions has an osmolality of 290 mOsM. These solutions are then mixed in the following amounts to give the following final concentrations:

| | Volume (ml) | final concentration (g/l) | final concentration (mM) |
|---|---|---|---|
| TMAO | 134.5 | 7.88 | 71 |
| raffinose | 215.5 | 62.5 | 124 |
| sodium sulphate | 150 | 5.5 | 38.7 |
| calcium chloride | 7 | 0.24 | 1.6 |

This gives a proportion of raffinose to TMAO to sodium sulfate of 1:0.62:0.70. For use with non-mammalian biological materials, the solutions may be made up to an osmolality between about 900 mOsM and about 1000 mOsM for marine materials, and between about 70 mOsM and about 80 mOsM for plant materials, and mixed in the same ratios.

A composition comprising raffinose, TMAO, sodium citrate and calcium chloride has also been found to be highly effective in the preservation of biological materials. In one embodiment, such solutions comprise, in an amount that is equiosmolar to the material to be preserved, raffinose and TMAO in a molar ratio greater than about 1.1:1 or less than about 2.0:1, preferably between about 1.1:1 and about 2.0:1, more preferably between about 1.4:1 and about 1.8:1, and most preferably of about 1.6:1; an equiosmolar amount, again to the material to be preserved, of sodium citrate; and greater than about 1.5 mM or less than about 2.0 mM, preferably between about 1.5 mM and about 2.0 mM, calcium chloride. Preferably, the calcium chloride is present at a concentration of about 1.75 mM, with the sodium citrate preferably being present in an amount greater than about 10% or less than about 30% by volume of a solution equiosmolar to the material to be preserved, more preferably between about 10% and about 30%. Preferably, the sodium citrate is present at a concentration greater than about 5 mM or less than about 20 mM, more preferably, between about 10 mM and about 20 mM.

In one embodiment, such solutions are made from stock solutions of TMAO, raffinose, sodium citrate and calcium chloride, each of which is equiosmolar to the material to be preserved. For example, for mammalian tissues of osmolality 0.29 OsM the stock solutions contain:

| | |
|---|---|
| TMAO dihydrate | 29.7 g/l |
| raffinose | 147.1 g/l |
| sodium citrate dihydrate | 29.0 g/l |
| calcium chloride dihydrate | 17.1 g/l |

The volumes of these solutions used and the final concentrations of the solutes are:

| | Volume (ml) | final concentration (g/l) | final concentration (mM) |
|---|---|---|---|
| TMAO | 173–134.6 | 10.2–7.9 | 91.9–71.7 |
| raffinose | 276–215 | 80.1–63.3 | 159–125 |
| sodium citrate | 50–150 | 2.9–8.7 | 9.9–17 |
| calcium chloride | 7 | 0.25 | 1.7 |

In another aspect, the inventive methods employ solutions comprising either betaine or trimethyl amine oxide, together with sodium citrate and sodium chloride, with the betaine or TMAO preferably being present at a concentration greater than about 150 mM or less than 220 mM, more preferably between about 150 mM and about 220 mM, and most preferably at a concentration of about 187 mM for betaine or about 184 mM for TMAO; the sodium citrate preferably being present at a concentration greater than about 1.5 mM or less than about 2.5 mM, more preferably between about 1.5 mM and about 2.5 mM and most preferably at a concentration of about 1.96 mM; and the sodium chloride preferably being present at a concentration greater than about 30 mM or less than about 60 mM, more preferably between about 30 mM and about 60 mM, and most preferably at a concentration of about 45.8 mM. As discussed in detail below, it has been found that these solutions are particularly effective in the preservation of platelets.

In yet another aspect, the inventive methods employ compositions comprising a Class II solute, preferably TMAO or betaine, in combination with sodium chloride and a calcium salt, preferably calcium chloride. In one embodiment, such compositions comprise equiosmolar to the material to be preserved sodium chloride and TMAO/betaine, together with calcium chloride at a concentration greater than about 1.5 mM or less than about 2.0 mM, more preferably between about 1.5 mM and about 2.0 mM, and most preferably about 1.75 mM. Preferably the solution comprises TMAO or betaine in amount of more than about 60% or less than about 80% by volume of a solution having the same osmolality as the material to be preserved, more preferably between about 60% and about 80% and most preferably about 70%. The sodium chloride is preferably present in an amount less than about 40% or greater than about 5% by volume or a solution having the same osmolality as the material to be preserved, more preferably in an amount between about 40% and about 20%, and most preferably at an amount of about 30%. The sodium chloride is preferably present at a concentration between about 30 mM and about 65 mM, more preferably at a concentration of between about 40 mM and about 50 mM, and most preferably at a concentration of about 46.8 mM. The concentration of sodium chloride in the inventive compositions is therefore significantly less than that in conventional saline-based media, which typically comprise 145 mM sodium chloride.

For the preservation of mammalian tissues of osmolality of 0.29 OsM, for example, such solutions may be prepared from stock solutions which contain, for example:

| | |
|---|---|
| TMAO dihydrate | 29.7 g/l |
| sodium chloride | 9.08 g/l |
| calcium chloride dihydrate | 17.1 g/l |

The volumes of these solutions used and the final concentrations of the solutes are:

| | Volume (ml) | final concentration (g/l) | final concentration (mM) |
|---|---|---|---|
| TMAO | 300–400 | 7.8–23.8 | 161–214 |
| sodium chloride | 200–100 | 3.6–1.82 | 62–31 |
| calcium chloride | 7 | .25 | 1.7 |

Unlike many methods typically used for the preservation of biological materials, the inventive methods do not employ conventional cryoprotectants, indeed the absence of conventional cryoprotectants at concentrations greater than about 5% is preferred, due to their often toxic side effects. As used herein, the term "conventional cryoprotectants" refers to two types of compounds. The first includes DMSO, glycerol, ethanol, methanol and propane-diol, which have high solubilities in water and diffuse passively across cell membranes. The second type of cryoprotectant consists of water-soluble polymers which cannot cross cell membranes. Examples of cryoprotectants of this type include polyethylene glycol (mw 8,000 or 20,000), polyvinyl pyrrolidone (mw 30,000), dextran (mw 10,000–500,000), Ficoll (mw 70,000) and hydroxyethyl starch.

The word "about," when used in this application with reference to temperature (°C.), contemplates a variance of up to 10° from the stated temperature. The word "about," when used in this application with reference to molecular weight, contemplates a variance of up to 10% from the stated molecular weight. The word "about," when used with reference to the solubility of a solute or molarity of a solution, contemplates a variance of up to 5% from the stated molarity. The word "about," when used with reference to a ratio, contemplates a variance of up to 0.2 on either side of the ratio. The word "about," when used with reference to a percentage solution composition, contemplates a variance of up to 10% from the stated percentage. The word "about," when used with reference to the osmolality of a solution, contemplates a variance of up to 10% from the stated osmolality.

The following examples are offered by way of illustration and not by way of limitation.

EXAMPLE 1

The efficacy of the inventive methods in the preservation of platelets was examined as follows.

Platelets were prepared from whole blood by centrifugation at 400 g for 7 minutes, collection of the platelet-rich plasma, and its centrifugation at 2900 g for 13 minutes. The platelet button was immediately resuspended at a concentration of $53 \times 10^9$/l in cold (4° C.) Solution 70/30c2, containing 45.8 mM NaCl, 184 mM TMAO and 1.96 mM sodium citrate at a total osmolality of 0.29 OsM. The cryovial was immediately plunged into liquid nitrogen. The lids of the cryovials were replaced quickly with perforated lids and the vials put in a precooled (−140° C.) flask and attached to a Flexi-Dry µP Freeze Dryer (FTS Systems, Stone Ridge, N.Y., USA) overnight. Vials were removed from the freeze dryer and the holes in the lids covered with parafilm "M" (American National Can$_{TM}$).

Figure 1B:
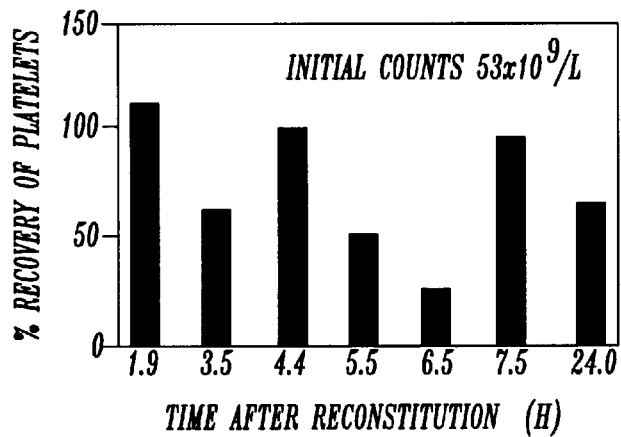

Freeze-dried platelets were stored at room temperature and subsequently reconstituted by adding the same volume of water (at 4° C.) that had been extracted during freeze drying, and then assayed for platelet counts and for spontaneous and thrombin-activated aggregation at different time intervals following reconstitution. The results of this study are shown in FIG. 1. After the shortest time interval of 1.9 hours, spontaneous aggregation was zero, thrombin-activated aggregation was over 80% and recovery 100%. After a time interval of 24 hours, both thrombin-activated aggregation and platelet recovery were greater than 50%.

EXAMPLE 2

The effectiveness of Solution 70/30c2 in the lyophilization of platelets as compared to plasma was investigated as follows.

Figure 2:
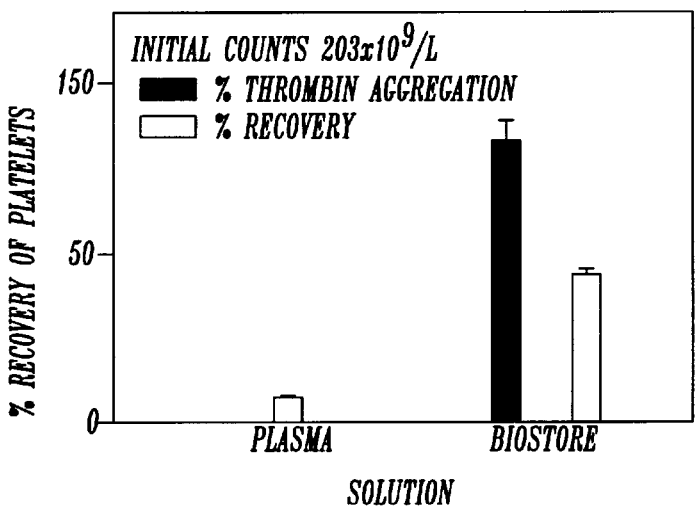
FIG. 2 illustrates the percentage recovery and percentage thrombin-activated aggregation of reconstituted platelets following lyophilization in either Solution 70/30c2 or plasma.

Platelets were prepared as described above in Example 1. Some were resuspended in Solution 70/30c2 ($203 \times 10^9$/l) and some in plasma ($452 \times 10^9$/l). 3.9 ml of each were put in 15 ml Falcon tubes and plunged into liquid nitrogen. The top of each tube was removed and replaced with parafilm with two holes pierced in it. Tubes were put in a precooled flask and attached to the Freeze Dryer overnight. On removal the holes were covered with fresh parafilm. Platelets were reconstituted by adding 3.9 ml water. Platelet counts and thrombin aggregation were determined as described above, with platelets in plasma being spun down and taken up in phosphate-buffered saline before measurement of thrombin aggregation. As shown in FIG. 2, the percentage recovery of thrombin aggregation was excellent in the platelets freeze dried in Solution 70/30c2 but not in platelets freeze dried in plasma. Recovery of platelet numbers in Solution 70/30c2 was also much greater than that in plasma.

EXAMPLE 3

This example illustrates the effectiveness of solutions of betaine, sodium chloride and sodium citrate in the lyophilization of platelets.

Platelets were prepared as described above in Example 1 and resuspended in a solution of 187 mM betaine, 45.8 mM sodium chloride and 1.96 mM sodium citrate at a concentration of $288 \times 10^9$/l before being rapidly frozen at −140° C. Samples were frozen at an angle so that there was a large surface area for sublimation but the frozen sample did not reach the top of the tube. Silica gel was cooled to −140° C. and placed in the lyophilization flask (also cooled to −140° C.) before adding the samples to be sublimed. After 20 hours at a pressure of approximately 200 mτ and a temperature of −80° C., the vacuum was slowly released and the tubes put in a dedicated desiccator containing dry silica gel.

Suspensions were reconstituted by adding the volume of water lost during lyophilization and inverting gently. Samples were reconstituted after various times over silica gel to give the recoveries shown in Table 1.

| Days in desiccator | Recovery from 288 × 10⁹/l initially |
| --- | --- |
| 0 | 4 × 10⁹ |
| 2 | 12,15 × 10⁹ |
| 4 | 24 × 10⁹ |
| 6 | 42 × 10⁹ |
| 15 | 87 |
| 17 | 70 |

These results indicate that drying was incomplete in the lyophiliser and continued during the time over silica gel. Similar results were obtained using Solution 70/30c2 in which a recovery of 45×10⁹/l after 2 days on silica gel gave a recovery of 200×10⁹/l after 16 days.

EXAMPLE 4

This example illustrates the effect of varying the concentration of betaine on the lyophilization of platelets.

Stock solutions of 0.29 OsM betaine, 0.29 OsM NaCl and 0.1M sodium citrate at pH 6.5, were mixed in the following proportions:

| betaine (ml) | NaCl (ml) | citrate (ml) | [betaine] (mM) | [NaCl] (mM) |
| --- | --- | --- | --- | --- |
| 70 | 30 | 2 | 187 | 45.8 |
| 60 | 40 | 2 | 160 | 61 |
| 50 | 50 | 2 | 133 | 76 |
| 40 | 60 | 2 | 106 | 92 |
| 30 | 70 | 2 | 80 | 107 |

Figure 8A:
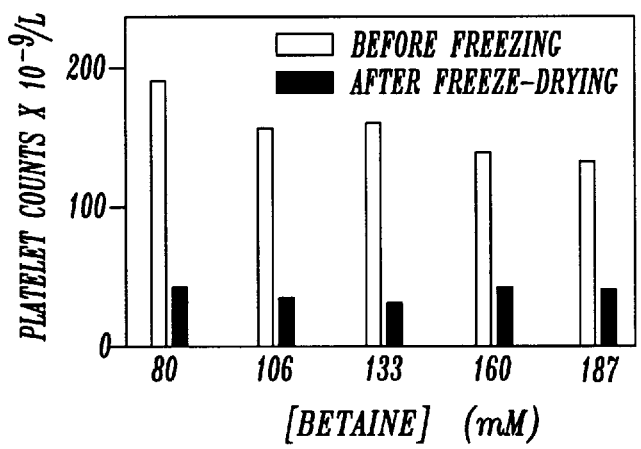
FIGS. 8A, B and C illustrate platelet counts, percentage recovery and percentage thrombin-activated aggregation, respectively, for reconstituted platelets following lyophilization in solutions of sodium citrate with varying concentrations of betaine and sodium chloride.
Figure 8B:
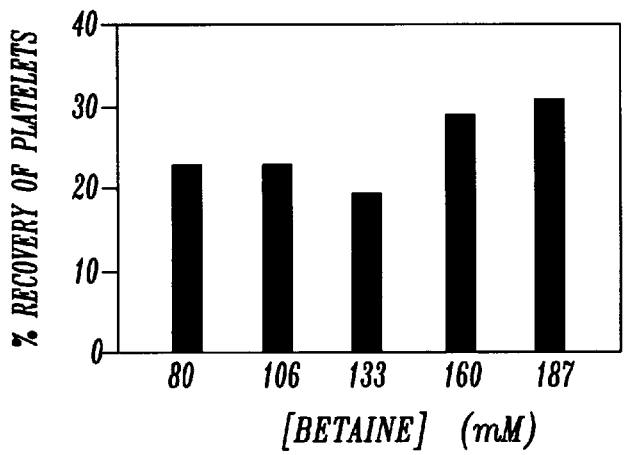
Figure 8C:
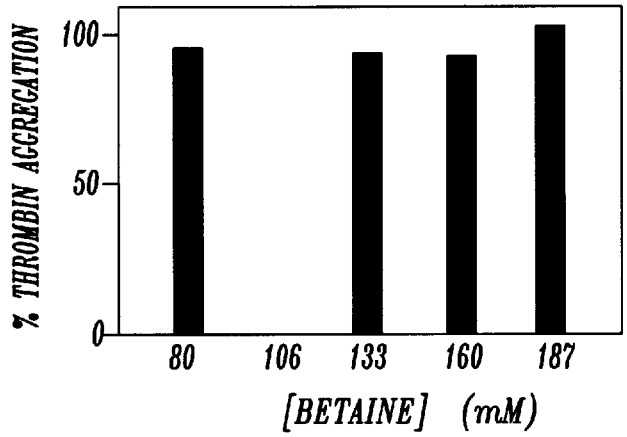

Platelets were prepared as described above in Example 1 and resuspended in the above solutions of betaine, sodium chloride and sodium citrate. Samples were lyophilised for 20 hours as described above in Example 3 and transferred to a desiccator containing silica gel. Samples were reconstituted after 7 days. Platelet counts, percentage recovery and percentage thrombin-activated aggregation on reconstitution are shown in FIGS. 8A, B and C, respectively. A percentage recovery of 30% was obtained with the highest concentration of betaine (187 mM), with the percentage of thrombin-activated aggregation being close to 100% for all concentrations of betaine. These percentage aggregations were all relatively fast, reaching a constant minimum within 4 minutes. This compares favorably with results obtained using the same solutions in freeze-thawing studies, suggesting that freeze-drying is a gentler process than storage at temperatures below freezing.

EXAMPLE 5

This example illustrates the effectiveness of the inventive lyophilization methods in the preservation of red blood cells.

Packed red blood cells (1 ml) were resuspended in 2 ml cold (4° C.) Solution 70/30B, containing 188 mM TMAO, 46.7 mM sodium chloride and 1.75 mM calcium chloride at a total osmolality of 0.29 OsM, in a 4.5 ml Nunc cryovial and immediately plunged into liquid nitrogen at −196° C. They were transferred to a precooled (−140° C.) flask and attached to the precooled Flexi-Dry μP Freeze Dryer and dried overnight. Freeze-dried cells were reconstituted with 2 ml water and 4 ml plasma. There was some haemolysis but numerous intact biconcave discs were recovered.

EXAMPLE 6

This example illustrates the efficacy of the disclosed preservation solutions in the storage of isolated platelets.

Blood was collected in EDTA and platelets isolated using standard centrifugation techniques. The final platelet-rich pellet was diluted into 50 ml of either plasma or $Ca^{2+}$-free Solution 70/30 (70% raffinose/TMAO (1.6:1), 30% $Na_2SO_4$). Eighty percent of platelets survived after 28 days of storage at 4° C. in $Ca^{2+}$-free Solution 70/30, compared to 50% survival in plasma. This survival rate after storage was significantly better than the five days for which platelets are typically held at 21° C.

Platelets are conventionally isolated from blood collected in citrate anticoagulant. In order to effectively preserve platelets prepared according to such methods, a preservative solution containing 45.8 mM NaCl, 184 mM TMAO and 1.96 mM sodium citrate at a total osmolality of 0.29 OsM was prepared (referred to as Solution 70/30c2). The effectiveness of this solution in the preservation of platelets at 4° C. was assessed by counting platelets and measuring their aggregation in response to stimulation by thrombin.

Preliminary experiments showed that storage in glass tubes coated with dichlorodimethyl silane stabilized platelets relative to storage in plastic or uncoated glass. In a first experiment, platelets were first processed in tubes and subsequently stored in Solution 70/30c2 in dichlorodimethyl silane-coated glass tubes at 4° C. Platelets were found to survive for 14 days with high levels of thrombin aggregation. In a second experiment, platelets were processed in plastic bags and transferred to a single dichlorodimethyl silane-coated glass bottle for storage at 4° C. in Solution 70/30c2. Platelet counts and thrombin aggregation levels remained high for 18 days. When platelets were stored in Solution 70/30c2 at 4° C. for long periods, the numbers of platelets remained high after 26 days but they responded less well to thrombin activation, suggesting that the plastic surface was unfavorable.

EXAMPLE 7

The efficacy of the disclosed solutions in the preservation of mouse embryos was tested as described below. As embryos consist of rapidly dividing cells, they are difficult to arrest, and therefore, provide a sensitive test of storage solutions.

Viable mouse embryos were stored for periods of 1, 2 or 3 days at 4° C. in either PBS or an aqueous solution of either raffinose, trehalose, sucrose or lactose (Class I solutes), together with a solute selected from the group consisting of trimethyl amine oxide (TMAO), betaine, taurine, sarcosine, glucose, mannose, fructose, ribose, galactose, sorbitol, mannitol, inositol and taurine (Class II solutes), at a ratio of Class I solute to Class II solute of 1.6:1. Each Class I/Class II solution also contained calcium sulfate at a concentration of 1.75 mM. The solutions also contained 0.1–1% bovine serum albumin (BSA) and 25 mg/L of kanamycin sulfate. All reagents were obtained from Sigma Chemical Company (St. Louis, Mo.). Survival of the embryos was assessed by subsequent culture in Dulbecco's Modified Eagles Medium (DMEM, Life Technologies, Grand Island, N.Y.) and was expressed both as the number of live embryos present after storage and the number of embryos which hatched after 48 hours in culture at 37° C.

A significant percentage of embryos hatched following storage for one day in most combinations of solutes, but following three days of storage a high percentage of hatching was only obtained with combinations of raffinose, trehalose or sucrose with TMAO. Raffinose was found to be the best Class I solute and TMAO the best Class II solute, with trehalose and betaine being the second best Class I and Class II solutes, respectively. The optimal total osmolality of the Class I/Class II solutions for preservation of mouse embryos was found to be 0.30 OsM.

Figure 3A:
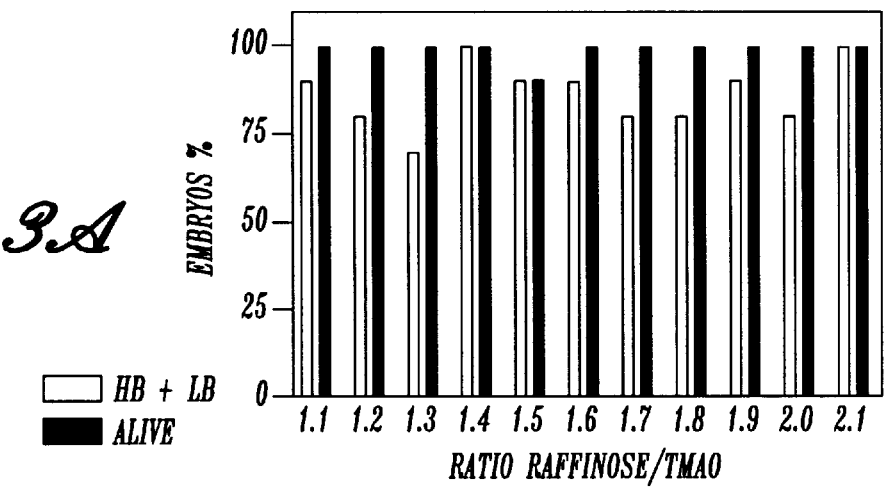
FIGS. 3A, B and C illustrate the survival of mouse embryos after storage for 1, 2 and 3 days, respectively, at 4° C. in aqueous solutions with varying molar ratios of raffinose to TMAO, with 1.75 mM $CaSO_4$.
Figure 3B:
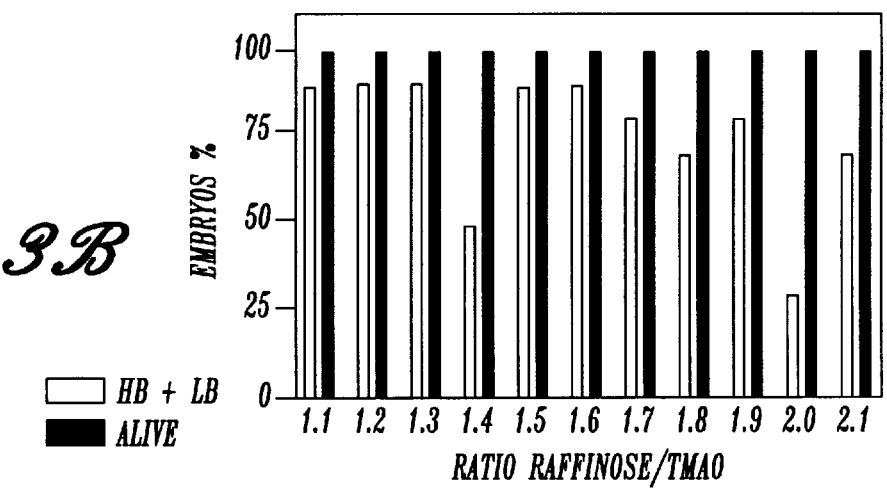
Figure 3C:
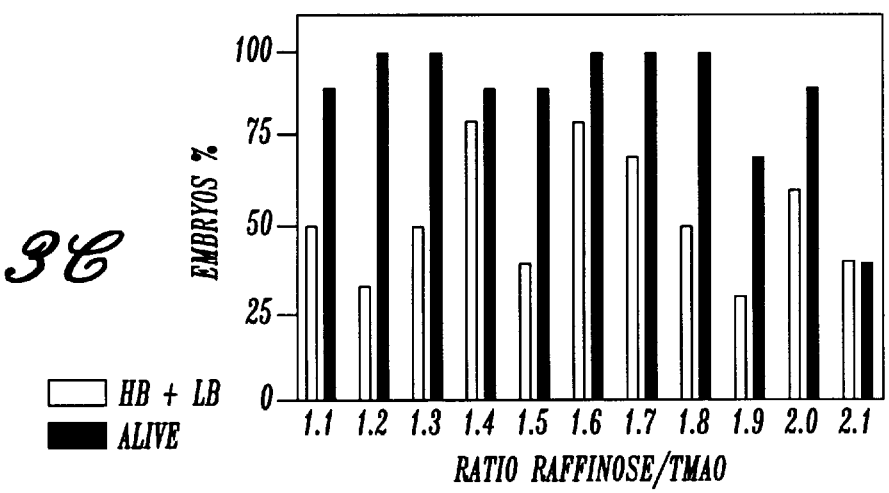

The three best combinations of Class I and Class II solutes were then retested to determine the optimal molar ratios of Class I to Class II solutes. The results of this study for raffinose and TMAO, with 1.75 mM $CaSO_4$, are shown in FIGS. 3A–C, with FIG. 3A illustrating survival after storage for 1 day, FIG. 3B illustrating survival after storage for 2 days and FIG. 3C illustrating survival after storage for 3 days. Of the three solutions tested, a raffinose:TMAO molar ratio of 1.6:1 resulted in the highest percentage of survival of embryos. The second highest percentage of survival was obtained with a trehalose:TMAO molar ratio of 1.3:1. The third highest percentage of survival was obtained with a raffinose:betaine molar ratio of 1.4:1.

Figure 4:
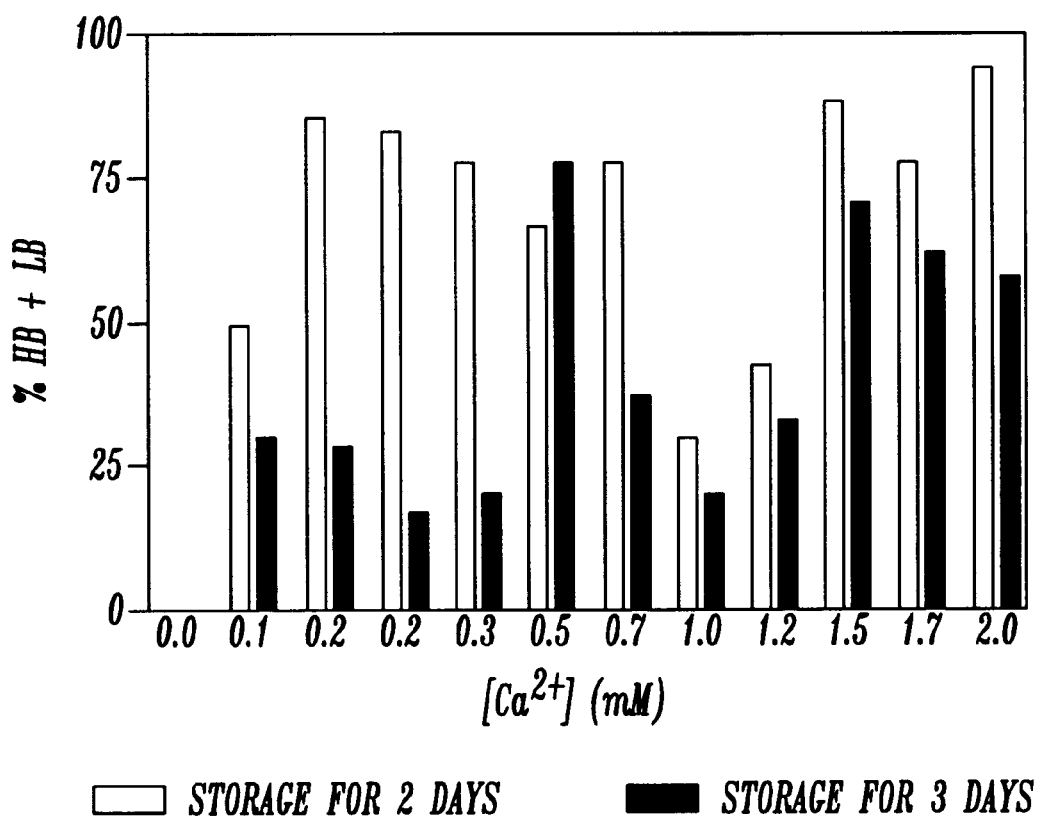
FIG. 4 shows the $Ca^{2+}$ dependence of mouse embryo survival following storage in raffinose/TMAO at 4° C. for 2 and 3 days.
Figure 5A:
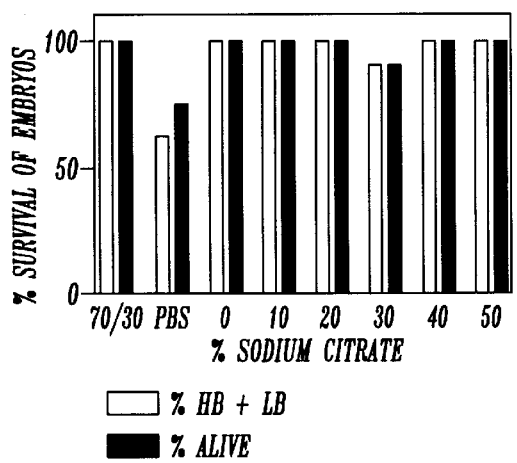
FIGS. 5A, B, C and D show the survival of mouse embryos following storage at 4° C. for 1, 2, 3 or 4 days, respectively, in either PBS, Solution 70/30, or a mixture of raffinose, TMAO, sodium citrate and calcium chloride.
Figure 5B:
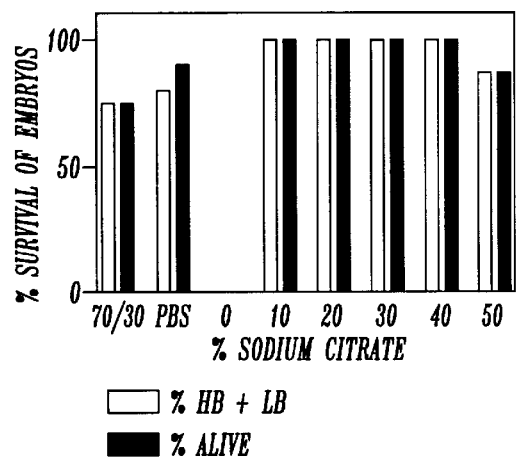
Figure 5C:
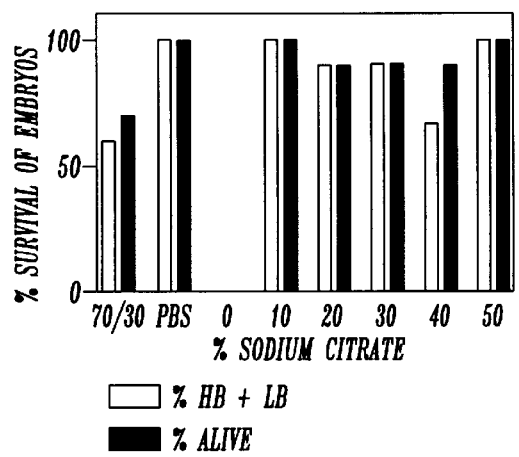
Figure 5D:
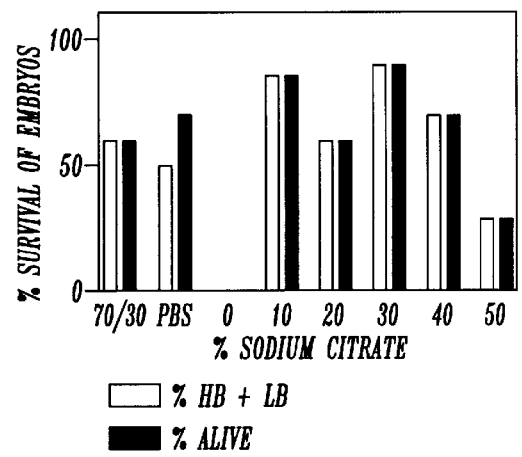
Figure 6A:
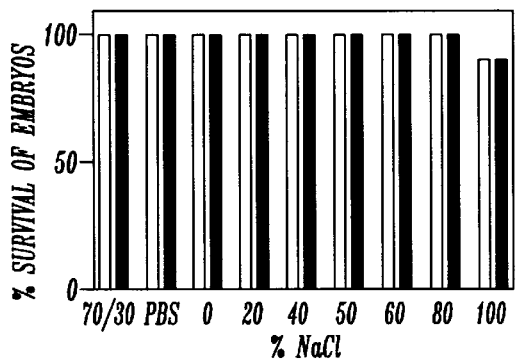
FIGS. 6A, B, C, D and E show the survival of mouse embryos following storage at 4° C. for 1, 2, 3, 4 or 5 days, respectively, in a range of mixtures of NaCl and TMAO plus calcium chloride.
Figure 6B:
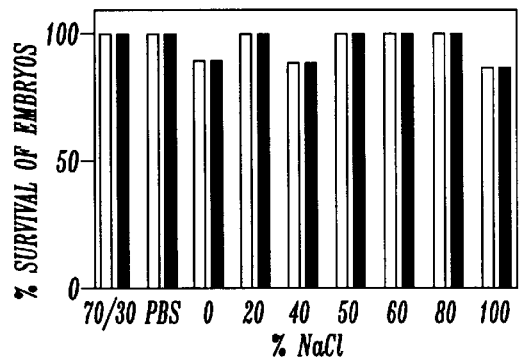
Figure 6C:
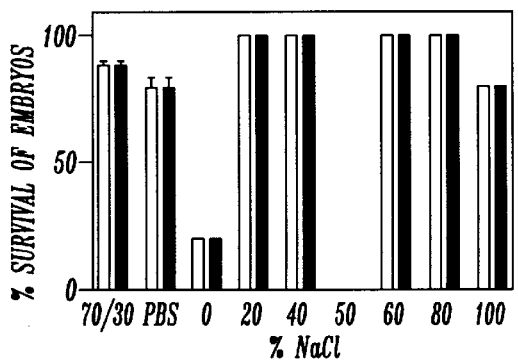
Figure 6D:
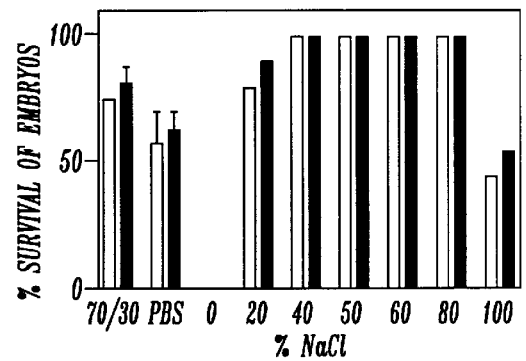
Figure 6E:
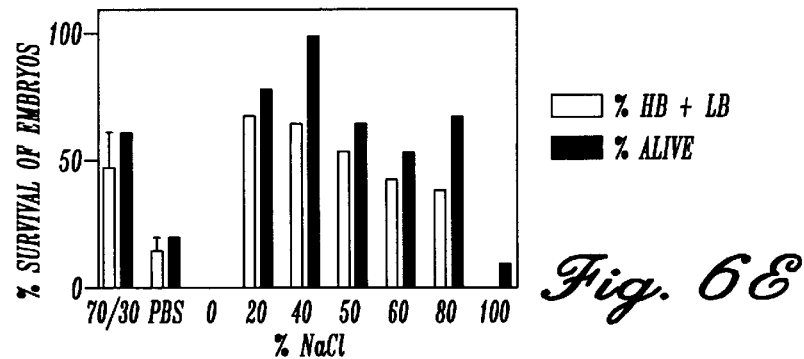

The percentage of embryos hatching following storage for 2 and 3 days at 4° C. in solutions containing a 1.6:1 molar ratio of raffinose to TMAO and varying concentrations of $Ca^{2+}$ is shown in FIG. 4. It was found that $Ca^{2+}$ is required for embryo preservation, with a non-linear concentration dependence. A $CaSO_4$ concentration of 1.75 mM was subsequently used with most biological materials. One exception was that of isolated platelets which were found to survive best in $Ca^{2+}$-free solutions.

A raffinose/TMAO 1.6:1 solution with 1.75 mM $CaSO_4$ was then mixed in different proportions with a solution of 0.30 OsM $Na_2SO_4$ containing 1.75 mM $CaSO_4$, and the percentage of mouse embryos hatching in culture following storage in these solutions for 1, 2 and 3 days at 4° C. was determined. The highest percentage of hatched embryos was obtained with 70% raffinose/TMAO (1.6:1), 30% $Na_2SO_4$ and 1.75 mM $CaSO_4$ (hereinafter referred to as Solution 70/30). The optimal osmolality appeared to be close to 300 mOsM. Solution 70/30 was subsequently used for many applications and proved to be an effective storage solution for many biological materials including bone marrow stem cells, hearts, red blood cells and osteoblasts. Solution 70/30 without $Ca^{2+}$ was found to be highly effective for the preservation of platelets.

In subsequent studies, mouse embryos were stored at 4° C. in a range of mixtures of equiosmolar solutions of sodium citrate and raffinose/TMAO, with the raffinose and TMAO being present at a ratio of 1.6:1. FIGS. 5A–D show the percentage of embryos that hatched in culture following storage in such solutions for 1, 2, 3 or 4 days, respectively, compared to those that hatched following storage in either PBS or Solution 70/30. These results indicate that solutions comprising sodium citrate, raffinose and TMAO may be more effective for long term storage of embryos than either PBS or Solution 70/30.

Figure 7:
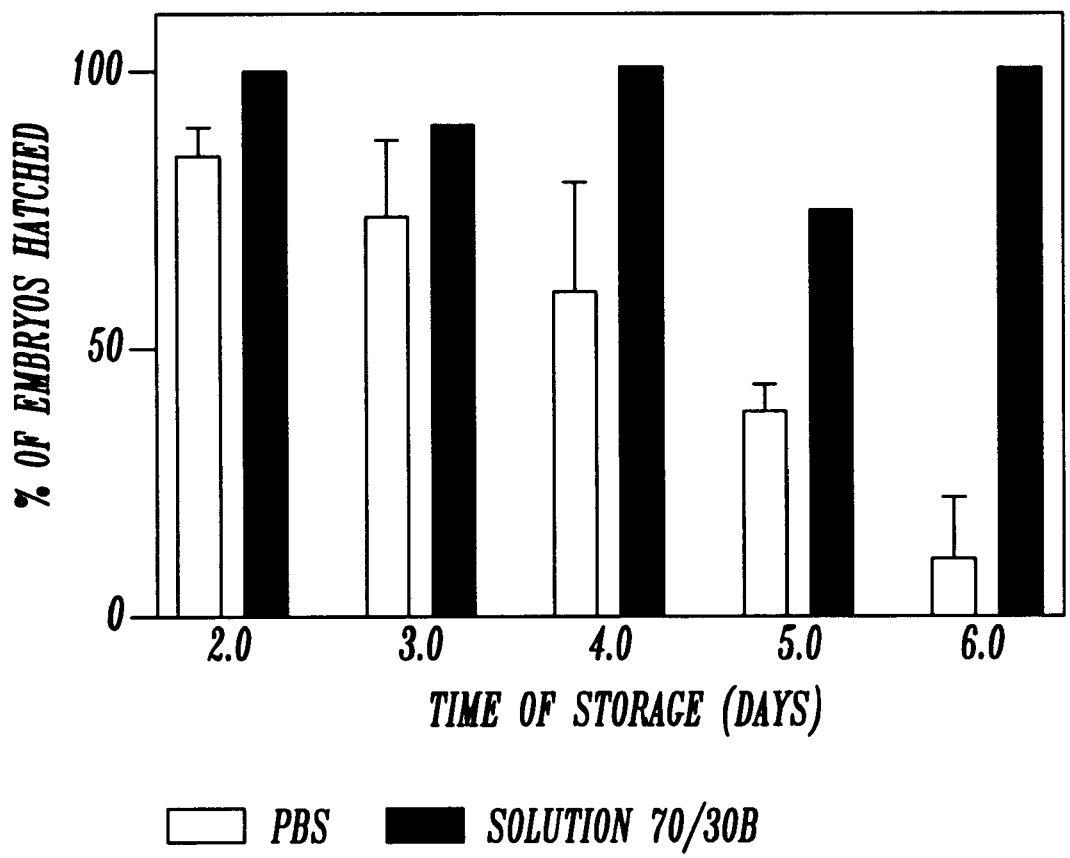
FIG. 7 shows the survival of mouse embryos following storage at 4° C. in either PBS or 30% NaCl/70% TMAO plus calcium chloride (referred to as Solution 70/30B).

FIGS. 6A–E show the percentage of mouse embryos that hatched after 3 days of culture at 37° C. following storage at 4° C. for 1, 2, 3, 4 or 5 days, respectively, in a range of mixtures of NaCl and TMAO plus calcium chloride. Solutions containing between about 20% and about 40% NaCl were found to be highly effective in preserving the viability of the embryos. FIG. 7 compares the results of storage of mouse embryos in 30% NaCl/70% TMAO plus 1.75 mM calcium chloride (referred to as Solution 70/30B) for up to 6 days at 4° C. with storage in PBS. These results demonstrate that Solution 70/30B is much more effective than PBS in preserving the viability of mouse embryos.

Although the present invention has been described in terms of specific embodiments, changes and modifications can be carried out without departing from the scope of the invention which is intended to be limited only by the scope of the appended claims.

I claim:

1. A method for the preservation of a biological material selected from the group consisting of platelets, platelet membranes and red blood cells, comprising:
   (a) contacting the biological material with a preservative solution, wherein the preservative solution consists essentially of betaine, sodium citrate and sodium chloride, the preservative solution being substantially isotonic with the biological material and substantially free of iodide, dihydrogen phosphate, bicarbonate, nitrate and bisulfate;
   (b) cooling the biological material to a temperature of less than about −140° C.; and
   (c) drying the biological material to provide a freeze-dried material.

2. The method of claim 1, wherein the biological material is cooled to a temperature of about −196° C.

3. The method of claim 2, wherein the biological material is cooled by immersion in liquid nitrogen.

4. The method of claim 1, wherein the freeze-dried material has a residual water content of less than about 5% by weight.

5. The method of claim 4, wherein the freeze-dried material has a residual water content of less than about 1% by weight.

6. The method of claim 1, wherein the biological material is dried under a vacuum.

7. The method of claim 1, wherein the preservative solution has an osmolality of about 280 mOsM to about 320 mOsM.

8. The method of claim 1, wherein the preservative solution is substantially free of DMSO, glycerol, ethanol, methanol, propane-diol, polyethylene glycol, polyvinylpyrrolidone, dextran, Ficoll and hydoxyethyl starch.

9. A method for the preservation of a biological material selected from the group consisting of platelets, platelet membranes and red blood cells, comprising:
   (a) contacting the biological material with a preservative solution, wherein the preservative solution comprises betaine at a concentration of about 150 mM to about 220 mM, sodium citrate at a concentration of about 1.5 mM to about 2.5 mM and sodium chloride at a concentration of about 30 mM to about 60 mM, the preservative solution being substantially isotonic with the biological material and substantially free of iodide, dihydrogen phosphate, bicarbonate, nitrate and bisulfate;
   (b) cooling the biological material to a temperature of less than about −140° C.; and
   (c) drying the biological material to provide a freeze-dried material.

10. The method of claim 9, wherein the preservative solution comprises betaine at a concentration of about 187 mM, sodium citrate at a concentration of about 1.96 mM and sodium chloride at a concentration of about 45.8 mM.

11. A method for the preservation of red blood cells, comprising:
   (a) contacting the biological material with a preservative solution, wherein the preservative solution comprises betaine and calcium chloride, the preservative solution being substantially isotonic with the red blood cells and substantially free of iodide, dihydrogen phosphate, bicarbonate, nitrate and bisulfate;

(b) cooling the biological material to a temperature of less than about −140° C.; and (c) drying the red blood cells to provide a freeze-dried material.

12. The method of claim 11, wherein the preservative solution additionally comprises sodium chloride.

13. The method of claim 12, wherein the preservative solution comprises betaine at a concentration of about 150 mM to about 220 mM, sodium chloride at a concentration of about 30 mM to about 65 mM and calcium chloride at a concentration of about 1.5 to about 2.0 mM.

14. The method of claim 13, wherein the preservative solution comprises betaine at a concentration of about 188 mM, sodium chloride at a concentration of about 46.8 mM and calcium chloride at a concentration of about 1.75 mM.

15. A freeze-dried material prepared according to the method of any one of claims 1, 9 and 11.

* * * * *